United States Patent
Ibach et al.

(10) Patent No.: US 10,983,064 B2
(45) Date of Patent: Apr. 20, 2021

(54) METHOD AND APPARATUS FOR DETERMINING THE CONCENTRATION OF AN ANALYTE IN A BODY FLUID

(71) Applicant: Roche Diabetes Care, Inc., Indianapolis, IN (US)

(72) Inventors: Alexander Ibach, Buehl (DE); Christian Ringemann, Mannheim (DE); Peter Stephan, Ilvesheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 115 days.

(21) Appl. No.: 15/777,493

(22) PCT Filed: Nov. 21, 2016

(86) PCT No.: PCT/EP2016/078299
§ 371 (c)(1),
(2) Date: May 18, 2018

(87) PCT Pub. No.: WO2017/089297
PCT Pub. Date: Jun. 1, 2017

(65) Prior Publication Data
US 2018/0328854 A1      Nov. 15, 2018

(30) Foreign Application Priority Data
Nov. 23, 2015 (EP) .................................... 15195934

(51) Int. Cl.
| | | |
|---|---|---|
| *C12Q 1/54* | (2006.01) |
| *G01N 21/84* | (2006.01) |
| *G01N 21/78* | (2006.01) |
| *C12Q 1/00* | (2006.01) |
| *G01N 21/77* | (2006.01) |

(52) U.S. Cl.
CPC ......... *G01N 21/8483* (2013.01); *C12Q 1/006* (2013.01); *C12Q 1/54* (2013.01); *G01N 21/78* (2013.01); *G01N 2021/7759* (2013.01)

(58) Field of Classification Search
None
See application file for complete search history.

(56) References Cited

U.S. PATENT DOCUMENTS

| | | |
|---|---|---|
| 4,373,818 A | 2/1983 | Yamamoto et al. |
| 9,255,286 B2 | 2/2016 | Horn et al. |
| 2007/0043519 A1* | 2/2007 | Zimmerle .......... G01N 21/8483 702/28 |

FOREIGN PATENT DOCUMENTS

| | | |
|---|---|---|
| JP | 1979-100794 A | 8/1979 |
| WO | 9918426 A1 | 4/1999 |
| WO | 2005036144 A1 | 4/2005 |
| WO | 2014037462 A1 | 3/2014 |

* cited by examiner

*Primary Examiner* — Michelle F. Paguio Frising
(74) *Attorney, Agent, or Firm* — Stinson LLP

(57) ABSTRACT

The invention concerns a method and an apparatus for determining the concentration of an analyte in a body fluid, where the following measures are proposed: providing a layered test element (12) including an enzyme-based chemistry layer which is responsive to the analyte by a color change, applying a sample of the body fluid onto the test element (12), detecting by means of a photometric reflectance measuring device (16) a reflectance value of the test element (12), correcting the measured reflectance value by a predetermined offset value attributed to the test element (12), determining a concentration value of the analyte using the offset-corrected reflectance value.

15 Claims, 2 Drawing Sheets

METHOD AND APPARATUS FOR DETERMINING THE CONCENTRATION OF AN ANALYTE IN A BODY FLUID

TITLE

Method and apparatus for determining the concentration of an analyte in a body fluid

CROSS REFERENCE TO RELATED APPLICATIONS

This application is a national phase application of PCT/EP2016/078299, filed Nov. 21, 2016, which claims priority to EP Patent Application Serial No. 15195934.3, filed Nov. 23, 2015, each of which are hereby incorporated by reference in their entireties.

The invention concerns a method for determining the concentration of an analyte in a body fluid, specifically the concentration of glucose in blood. The invention further concerns an apparatus adapted for carrying out such measurements and a corresponding system including said apparatus and the disposable test material.

BACKGROUND OF THE INVENTION

The document EP-A 2 618 160 discloses a test procedure using analytical test fields on a test tape, wherein a control value is determined from a from a time-variant change of measurement signals on the test field that is provided for sample liquid application, and wherein the measurement is discarded as erroneous when the control value falls below a preset threshold. In this context, it is proposed to determine the glucose concentration from a relative remission value that is calculated as a quotient of an end value of the reflectance and an initial dry value. In order to account for a signal offset of the device, which is independent of the test field, a calibration measurement on a black field is further proposed. However, this does not account for the influence of ambient conditions, e.g. high temperatures and humidity during storage of the test material. In this connection, it was only proposed to implement a failsafe against false interpretation of sample application.

BRIEF DESCRIPTION OF THE INVENTION

On this basis the object of the invention is to further improve the known methods and devices and to provide measures for superior accuracy of measurement even under varying production and storing conditions of the test material specifically for self-testing glucose measurement systems.

The combination of features stated in the independent claims is proposed to achieve this object. Advantageous embodiments and further developments of the invention are derived from the dependent claims.

The invention is based on the idea of taking into account an offset which is independent of the device, but specific of the used test element. Accordingly it is proposed according to the invention that the method mentioned at the outset comprises the steps of
a) providing a layered test element including an enzyme-based chemistry layer which is responsive to the analyte by a color change,
b) applying a sample of the body fluid onto the test element,
c) detecting by means of a photometric reflectance measuring device a reflectance value of the test element,
d) correcting the measured reflectance value by a predetermined offset value attributed to the test element,
e) determining a concentration value of the analyte using the offset-corrected reflectance value.

In this way, it is possible to correctly account for a limitation of the range of measurable reflectance values on a test element, which is not spanning from zero to the initial blanc reflectance value, but is scaling down to a lower limit given by the offset value. Then, in more refined steps, it is also possible to cancel out effects which are due to environmental stress (temperature, humidity) on the test elements.

According to a preferred embodiment, the offset value use for measurement correction is characteristic of a structure of the test element and independent of the color change. Such an offset can be clearly separated from instrument offsets which do not depend on variation of the test material.

Advantageously, the offset value is predetermined as an asymptotic level of a reference curve of reflectance versus analyte concentration at high concentration. This allows to find the lower level of the measuring range with a simple extrapolation.

It is also preferred that the offset value is calculated from a reflectance curve measured on reference material of test elements by means of a reference instrument. In this way, the offset value can be predetermined and fed into the measuring device.

According to a preferred implementation, said correcting includes subtracting the offset value from the measured reflectance value, such that the real signal level is taken into account.

For further measurement improvement it is advantageous to detect a blanc value of the reflectance on the dry test element before applying the sample, then to correct the blanc value by the predetermined offset value attributed to the test element, and finally to determine the analyte concentration value using the offset-corrected blanc and reflectance values. In this connection, it is also favorable when the blanc value is corrected by subtracting the predetermined offset value, and when a relative remission value is calculated from a quotient of the offset-corrected reflectance value and blanc value for determining the concentration value of the analyte. Thereby, all influencing factors which are not due to an additive deviation will be cancelled out.

Advantageously the concentration value of the analyte is determined in accordance with a correlation code which is stored in the device preferably in the form of a parameterized polynomial or lookup-table. Thereby, an unambiguous assignment of target values can be achieved.

For further consideration of possible variations it is advantageous to calibrate the photometric reflectance measuring device in the stage of production in order to zero a measuring offset characteristic of the device.

A particular embodiment further comprises determining a reflectance gain factor of the device by means of a reflectance standard, e.g. an internal or external white field.

Another convenience improvement provides that the test element is provided on a flat test strip or on a carrier tape rolled on a spool.

Another aspect of the invention concerns an apparatus for determining the concentration of an analyte in a body fluid, particularly a blood glucose meter, comprising
a) a housing adapted to receive a layered test element including an enzyme-based chemistry layer which is responsive to the analyte by a color change,
b) a measuring site for receiving the test element and applying a sample of the body fluid thereon, c) a photometric reflectance measuring device for detecting a reflectance value of the test element,
d) a correcting means adapted to correcting the measured reflectance value by a predetermined offset value attributed to the test element,
e) an evaluation unit for determining a concentration value of the analyte using the offset-corrected reflectance value.

In regard to an analytical system for determining the concentration of an analyte in a body fluid it is advantageous when the apparatus according to the invention is used in connection with at least one layered test element which is received in the apparatus and includes an enzyme-based chemistry layer which is responsive to the analyte by a color change.

DRAWINGS

The invention is further elucidated in the following on the basis of an embodiment example shown schematically in the drawings, where FIG. 1 is a perspective view of a blood glucose meter receiving a test strip and including an offset correcting means;

DETAILED DESCRIPTION OF THE INVENTION

Figure 1:
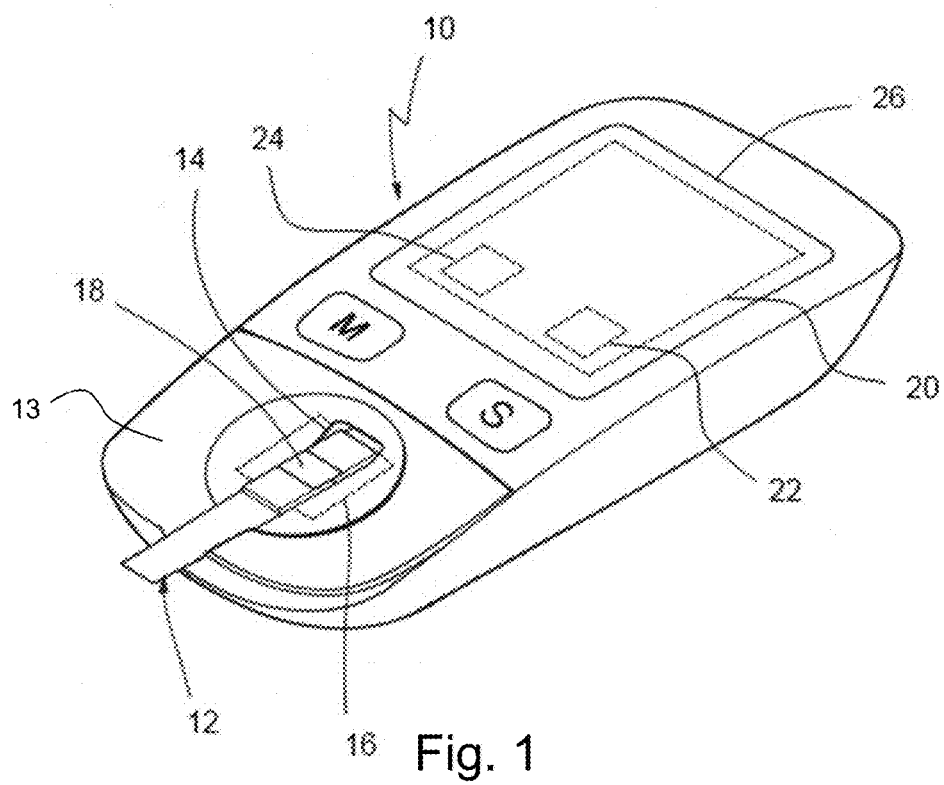

FIG. 1 schematically illustrates a photometric reflectance measuring device designed as handheld blood glucose meter 10 for insertion of a disposable test strip 12. The meter 10 comprises a housing 13 with a port 14 to position the test strip 12 in the optical path of a reflection photometer 16 to read the reflectance of an analytical test pad 18 of the strip 12. A small volume of a blood sample can be applied to the upper surface of the test pad 18, which has at least one chemistry layer wherein an enzyme-based reagent reacts with an analyte, specifically glucose leading to a change in color and hence in reflectance. The change in reflectance over a predetermined time period as a result of formation of reaction product is then related to the amount of analyte in the sample. This can be detected through the transparent bottom layer of the test pad 18 with the photometer 16 comprising a light source and a light sensor arranged in a reflection path for diffuse reflection of light (not shown). It is also possible to conduct such measurements using tape cassettes, where a number of test elements are provided on a carrier tape rolled on a spool.

The meter 10 further comprises a processing unit 20 including a correcting means 22 adapted to correct the measured reflectance value by subtracting a predetermined offset value which is characteristic of the test strip 12 and independent of the color change.

Then, the glucose concentration can be determined in an evaluation unit 24 using the offset-corrected reflectance value. The result is provided directly to the user on a display 26 of the device 10.

Figure 2:
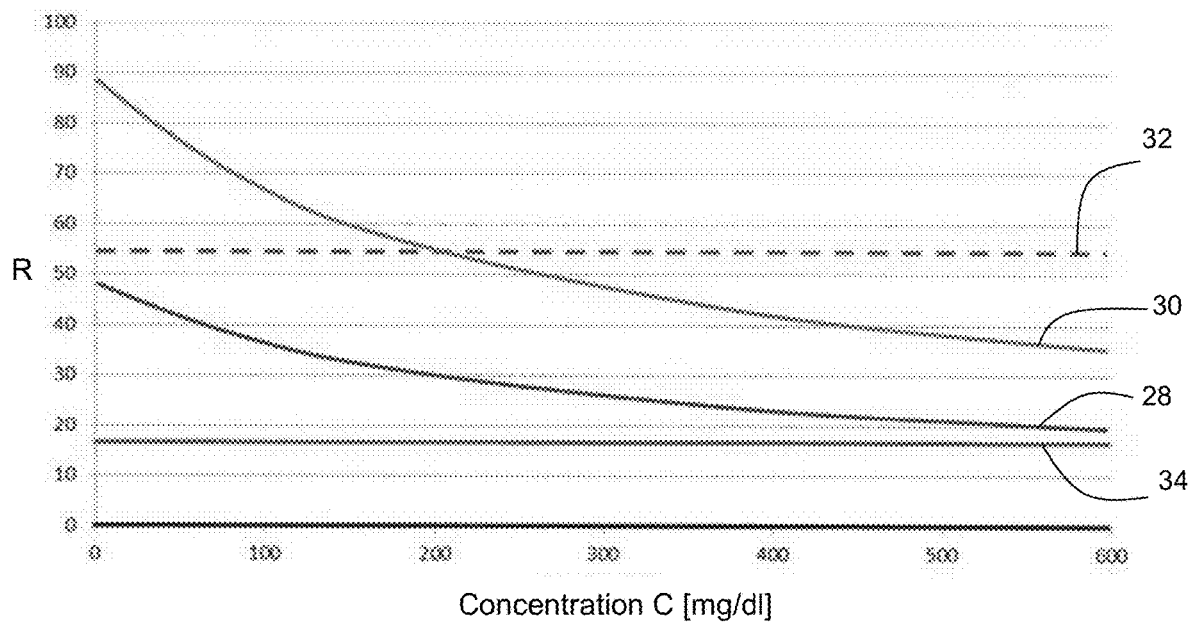
FIG. 2 is a diagram of reflectance versus concentration including a dry blanc value and an offset value.

FIG. 2 shows a reflectance curve 28 which unambiguously assigns to each glucose concentration C a reflectance reading R. With increasing glucose concentration, the color of the test pad 14 changes from light to dark, and thus the remission R decreases. In order to compensate for eventual device fluctuations, it is known to calculate the relative remission R % as follows:

$$R\% = R/B [\%] \qquad (1)$$

In equation (1), B denotes a blanc value of the reflectance which can be measured on the dry test strip 12 before applying the sample. Accordingly, the remission curve 30 has been drawn in FIG. 2 based on a constant blanc value 32.

A prerequisite for relying on relative remission values is that the absolute reflectance curve 28 tends to zero at high concentrations. On closer inspection the inventors have observed that an offset value 34 which significantly deviates from zero remains at high concentrations. Without wishing to be tied to any specific theory, a possible explanation for the offset may be found in reflections of measurement light on layer boundaries of the test pad 18, which are not influenced by color formation.

To account for this offset, equation (1) changes to $$R\% = (R+O)/(B+O) [\%], \qquad (2)$$

where O denotes the offset value and R, B are the real reflectance and blanc values deviating from the measured values. As can be seen from equation (2), the offset is not cancelled out in the quotient of the relative remission.

Consequently, in order to derive the actual reflectance and blanc values, the offset value O has to be subtracted from the measured values, which are obtained as counts of an A/D-converter in the detector.

In a more elaborate approach, the relative remission R % is described by parameters which depend on the condition of the test element 12 as well as on the state of the measuring device according to the following equation:

$$R\% = (k_d*(k_s*R+O_s)+O_d)/(k_d*(k_s*B+O_s)+O_d) \qquad (3)$$

In equation (3), $k_d$ denotes a varying gain factor of the device e.g. due to staining or scratching of optical elements or fluctuation of the light source and $k_s$ denotes a gain factor of the test strip e.g. due to a discoloration in the unused state. Further, $O_d$ indicates a device-specific offset which is observed without real measuring signal, and $O_s$ indicates a test strip specific offset value corresponding to O in equation (2).

It is possible to determine the gain factor $k_d$ of the device 10 by means of a reflectance standard, e.g. a white field which can be provided on the test strip 12. Then, $k_d = R_w/R_s$, where $R_w$ is the reflectance measured on the white field and $R_s$ is a nominal reflectance value.

Purposively, the device-specific offset $O_d$ is zeroed by calibration in a production stage of the device 10. In this case, all reflectance deviations which are specific to the device 10 are arithmetically eliminated in equation (3). However, this does not apply for strip-specific deviations.

Figure 3:
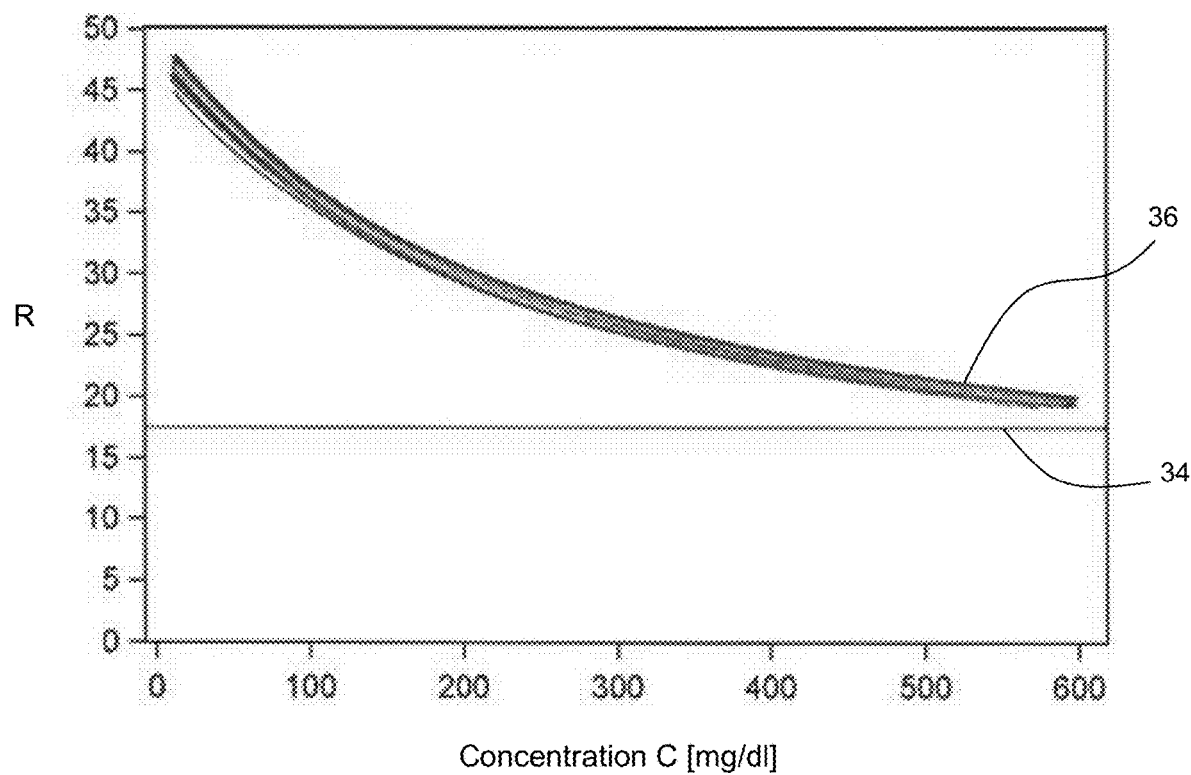
FIG. 3 shows concentration-dependent reflectance curves of different production batches of test strips.

FIG. 3 shows reference curves 36 of the reflectance R over glucose concentration C taken by a reference instrument on a large number of reference batches of test strips. As apparent from the curve shapes at high concentration, it is possible to determine a common test strip specific offset value $O_s$ as an asymptotic level of the reflectance curves. This can be done e.g. by spline extrapolation to receive an offset value $O_s$ of 17.5 in the given case.

In real measurements on the spot, the predetermined offset value $O_s$ can be subtracted from the measured reflectance value R and from the measured blanc value B. In this case, it is not necessary to determine $k_s$, as this factor is then correctly cancelled out in equation (3). Thus, test strip deviations due to ambient storing conditions e.g. humidity and temperature have no influence on the determined relative remission. This would not be the case when using the simple approach of equation (1).

The procedure described above allows to establish a correlation code for the glucose concentration which is corrected for the offset value $O_s$. Such a code can be implemented in the device 10 e.g. in the form of a parameterized polynomial $$C(R\%)=a+b*R\%+c*R\%^2+d*R\%^e+f*\exp(R\%^g) \quad (4)$$

wherein a,b,c,d,e,f,g are parameters determined from reference measurements, R % is the offset-corrected remission and C is the correlated glucose concentration.

The invention claimed is:

1. A method for determining the concentration of an analyte in a body fluid, using an apparatus comprising a meter configured to measure the reflectance of a test element, the meter in communication with a processor, comprising the steps of
    a) providing a layered test element (12) including an enzyme-based chemistry layer which is responsive to the analyte by a color change,
    b) applying a sample of the body fluid onto the test element (12),
    c) detecting by means of a photometric reflectance measuring device (16) a reflectance value of the test element (12),
    d) correcting the measured reflectance value by a predetermined offset value attributed to the test element (12), wherein the offset value is predetermined as an asymptotic level of a reference curve (36) of reflectance versus analyte concentration at high concentration, wherein the reference curve is measured on reference material of test elements (12) by means of a reference instrument,
    e) determining a concentration value of the analyte using the offset-corrected reflectance value,
    wherein steps d) and e) are performed using the processor.

2. The method of claim 1, wherein the offset value is characteristic of a structure of the test element (12) and independent of the color change.

3. The method according to claim 1, wherein said correcting includes subtracting the offset value from the measured reflectance value.

4. The method according to claim 1, further comprising detecting a blank value of the reflectance on the dry test element (12) before applying the sample, correcting the blank value by the predetermined offset value attributed to the test element (12), and determining the analyte concentration value using the offset-corrected blank and reflectance values.

5. The method of claim 4, wherein the blank value is corrected by subtracting the predetermined offset value.

6. The method of claim 4, wherein a relative remission value is calculated from a quotient of the offset-corrected reflectance value and offset-corrected blank value for determining the concentration value of the analyte.

7. The method according to claim 1, wherein the concentration value of the analyte is determined in accordance with a correlation code which is stored in the measuring device (16) optionally in the form of a parameterized polynomial or lookup-table.

8. The method according to claim 1, further comprising calibrating the photometric reflectance measuring device (16) in the stage of production in order to zero a measuring offset characteristic of the device.

9. The method according to claim 1, further comprising determining a reflectance gain factor of the device by means of a reflectance standard.

10. The method according to claim 1, wherein the test element (12) is provided as a flat test strip or on a carrier tape rolled on a spool.

11. An apparatus for determining the concentration of an analyte in a body fluid comprising:
    a) a housing adapted to receive a layered test element (12) including an enzyme-based chemistry layer which is responsive to the analyte by a color change,
    b) a measuring site (14) for receiving the test element (12) and applying a sample of the body fluid thereon,
    c) a photometric reflectance measuring device (16) for detecting a reflectance value of the test element (12),
    d) a processor (20) adapted to correct the measured reflectance value by a predetermined offset value attributed to the test element (12), wherein the offset value is predetermined as an asymptotic level of a reference curve (36) of reflectance versus analyte concentration at high concentration, wherein the reference curve is measured on reference material of test elements (12) by means of a reference instrument, and
    e) the processor (20) operable for determining a concentration value of the analyte using the offset-corrected reflectance value.

12. The apparatus according to claim 11, wherein the processor determines the concentration value of the analyte in accordance with a correlation code which is stored in the measuring device (16) in the form of a parameterized polynomial.

13. The apparatus according to claim 12, wherein the parameterized polynomial is expressed as $C(R\%)=a+b*R\%+c*R\%^2+d*R\%^e+f*\exp(R\%^g)$ wherein a, b, c, d, e, f, g are parameters determined from reference measurements, R % is the offset-corrected remission, and C is the correlated glucose concentration.

14. The apparatus according to claim 11, wherein the processor determines the concentration value of the analyte in accordance with a correlation code which is stored in the measuring device (16) optionally in the form of a lookup-table.

15. A system for determining the concentration of an analyte in a body fluid, particularly a blood glucose instrument, comprising an apparatus (10) according to claim 11 and at least one layered test element (12) which is received in the apparatus and includes an enzyme-based chemistry layer which is responsive to the analyte by a color change.

* * * * *